United States Patent
Zimba et al.

(10) Patent No.: US 7,943,142 B2
(45) Date of Patent: May 17, 2011

(54) EUGLENOID DERIVED ALKALOID

(75) Inventors: Paul V. Zimba, Corpus Christi, TX (US); Kevin R. Beauchesne, Hollywood, SC (US); Peter D. Moeller, James Island, SC (US); Richard E. Triemer, Okemos, MI (US)

(73) Assignees: The United States of America as represented by the Secretary of Agriculture, Washington, DC (US); Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 12/566,884

(22) Filed: Sep. 25, 2009

(65) Prior Publication Data
US 2010/0081571 A1   Apr. 1, 2010

Related U.S. Application Data

(60) Provisional application No. 61/100,874, filed on Sep. 29, 2008.

(51) Int. Cl.
*A01N 43/40*   (2006.01)
*A01P 13/00*   (2006.01)
*C07D 211/22*   (2006.01)
*C12P 17/12*   (2006.01)

(52) U.S. Cl. ............... 424/195.17; 504/155; 435/122; 546/248

(58) Field of Classification Search ............... 424/195.7; 504/155; 435/122; 546/248
See application file for complete search history.

(56) References Cited

U.S. PATENT DOCUMENTS

2006/0111557 A1   5/2006   Burkholder et al.
2008/0248956 A1*  10/2008  Kang et al.

OTHER PUBLICATIONS

Zimba, Paul V., et al., "Identification of euglenophycin—A toxin found in certain euglenoids", Toxicon(2009),doi:10.1016/j.toxicon. Jul. 4, 2009, published by Elsevier Ltd.
Zimba, P.V., et al., "Identification of euglenoid algae that produce ichthyotoxin(s)", Journal of Fish Diseases, 2004, 27, 115-117.

* cited by examiner

*Primary Examiner* — Michele C. Flood
(74) *Attorney, Agent, or Firm* — Albert Y. Tsui; John Fado; Lesley Shaw

(57) ABSTRACT

Disclosed herein is a purified toxin isolated from *Euglena sanguinea*. More specifically the toxin, termed euglenophycin, is an alkaloid having herbicidal and cytotoxicity against plant and mammalian cells.

8 Claims, 3 Drawing Sheets

EUGLENOID DERIVED ALKALOID

CROSS-REFERENCE TO RELATED APPLICATION

This present application claims priority under 35 U.S.C. §119(e) to U.S. Provisional Ser. No. 61/100,874, which was filed on Sep. 29, 2008, the application is hereby incorporated by reference.

FIELD OF THE INVENTION

This invention relates to a purified toxin derived from *Euglena sanguinea*. More specifically the toxin, termed euglenophycin, is an alkaloid having herbicidal and cytotoxicity against plant and mammalian cells.

BACKGROUND OF INVENTION

Many factors have been documented that can contribute to mortalities observed in finfish aquaculture including disease and harmful algal blooms of cyanobacteria, in addition to more common issues with oxygen stress or nitrogen toxicosis. The source, occurrence, and epidemiology of many freshwater, estuarine, and marine toxins produced by algae are well known. For instance, divisions of photosynthetic plankton are known to produce toxins that include but are not limited to Bacillariophyceae, Pyrrophyta, Prymnesiophyta, Raphidophyta, as well as certain members of the cyanoprokaryota. Impacts from these toxins are dependant on the affected organism, as well as route, concentration, and duration of exposure.

While cyanoprokaryotic algae, diatoms, prymnesiophytes, dinoflagellates, euglenoids, and rhaphidophytes are long known to produce algal toxins, the identification of a toxic euglenoid is unexpected given that this species of *Euglena* that was identified by Ehrenberg in the 1830s has presented no conclusive evidence of toxin production. An exception would be a tilapia-kill event detailed in Xavier M B, et al., 1991. *Algological Studies*, 62:133-142, wherein tilapia exposed to a *Euglena sanguinea* bloom in aquaria had euglenoid cells associated with gills, resulting in distressed breathing as manifested by surface porpoising and minor tilapia fish mortality.

*Euglena* form protective cyst when subjected to hostile environments as a survival mechanism. This formation contributes to the difficulty in recognizing toxins produced by *euglena* as these cells encyst when water is turbulent. Other environmental factors contribute to difficult toxin identification. One scenario is that a surface scum of the euglenoid forms in calm weather during mid-morning to afternoon, resulting in high concentrations of toxin in several centimeters thickness of water. Wind events would result in dissipation of the scum through encystment, leaving a surface microlayer containing dissolved toxins. Aquacultured fish are then fed floating feeds, resulting in concentrated exposure. These events lead to an increased difficulty in identifying a euglenophycin as the source of a toxin.

While cyanoprokaryotic algae, diatoms, prymnesiophytes, dinoflagellates, euglenoids, and rhaphidophytes are long known to produce algal toxins, euglenoid algae that produce toxins were isolated from aquaculture ponds, with toxin confirmation based on positive fish bioassays following exposure to the isolated clonal algal cultures. It remains an open question as to the isolation of toxin from euglenoid algae blooms at freshwater facilities.

Furthermore, while taxonomists have recognized the presence of euglenoid algae in both freshwater and marine systems, the lack of unique pigment biomarkers have prevented routine monitoring using remote sensing methodologies or HPLC pigment biomarker identification would lead to underestimation of importance of the division. Additionally, since the existence of a euglenoid toxin was only recently reported many previous fishkills caused by unidentified biological agents could be attributable to euglenoids. The apparent potency of this compound strongly suggests further assessment of occurrence in potable waters.

BRIEF SUMMARY OF THE INVENTION

Disclosed herein is a toxin composition. The toxin composition is obtained from euglenoid algae isolates. The compound has a structure similar to alkaloids produced by fire ant venom. Advantageously, the purified toxins produced by these euglenoid isolates have activity against cancerous cell lines. Toxicity was observed in euglenoid clonal culture isolates obtained from the pond as well as a clonal, culture collection taxon. The euglenoid toxin, derived from *Euglena sanguinea* are grown in batch culture wherein the toxin is recovered and purified by techniques which are well known to those skilled in the art.

Also disclosed herein is a purified bioactive euglenophycin composition isolated from from *Euglena sanguinea* having the structure:

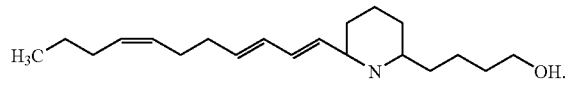

In one embodiment of the invention the euglenophycin is toxic against plant and mammalian cells. The compound is an alkaloid with a molecular weight of from about 288 Da to about 306 Da. In another embodiment of the invention, the euglenophycin is a herbicide and is toxic against algal cells.

Further disclosed is a method of controlling undesirable algal bloom, the method comprising contacting waterways with a herbicide composition having the formula:

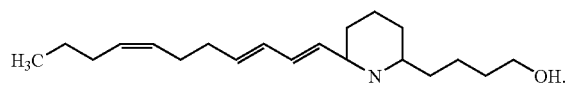

In one embodiment the herbicide is present in a concentration range of about 0.3 mg per liter to about 30 mg per liter. In another embodiment, the herbicide is effective against undesirable algal bloom such as *Microcystis aeruginosa* (cyanobacteria), *Planktothrix* (cyanobacteria), *Gomphonema parvum* (diatom), *Scenedesmus dimorphus* (green algae), and *Oocystis polymorpha* (green algae).

As disclosed is a method of isolating and purifying a euglenophycin, the method comprising culturing *Euglena sanguina* in a growth media to produce a euglenophycin therein, extracting *Euglena sanguina* cells by separating a fraction of organic compounds from said growth media by a gradient elution of using water and acetone, and separating the gradient using a by chromatography with porous silica beads. In one embodiment, the fractions are separated by a gradient of 90:10 water:acetone for 2 minutes then 20 minutes of 100% acetone. In another embodiment of the invention the said porous silica beads are Iatrobeads.

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

The invention provides a novel toxin composition. This toxin composition is obtained from *Euglena sanguinea*. *Euglena sanguinea* has been identified as the dominant alga present in a number of fish kill events since 2004. Since this discovery, toxic bloom events have occurred in a number of states, including North Carolina, South Carolina, Texas, Arkansas, and Mississippi. Over 400 grams (wet weight) of *Euglena* cell pellet were produced for subsequent toxin isolation and purification from the North Carolina clonal isolate. Microscopic analyses confirmed the purity of the cell pellet with the only alga present being *E. sanguinea*. The *E. sanguinea* derived toxin has been identified on the basis of toxicity towards GH4C1 rat pituitary cells.

DEFINITIONS

As used in the specification and claims, the singular form "a", "an" and "the" include plural references unless the context clearly dictates otherwise. For example, the term "a cell" includes a plurality of cells, including mixtures thereof.

The term "Euglenophyceae" refers to a group of unicellular colorless or photosynthetic flagellates found living in freshwater, marine, soil and parasitic environments. The class is characterized by solitary unicells, wherein most are free-swimming and have two flagella (one of which may be non-emergent) arising from an anterior invagination known as a reservoir. About 1000 species have been described and classified into about 40 genera and 6 orders. Examples of Euglenophyceae include, but are not limited to, the following genera: *Eutreptiella, Euglena* and *Tetruetreptia*. The species *Euglena sanguinea* is characterized as spindle, cylindrical or band-form in shape and having pellicle usually marked by longitudinal or spiral striae; some with a thin pellicle highly plastic; stigma usually anterior; chloroplasts discoid, band-form, or fusiform; two paramylum bodies located on either side of nucleus, rod-like to ovoid in shape or numerous and scattered throughout; contractile vacuole near reservoir.

The term "substantially pure chemical compound", as used in this specification and claims, refers to a chemical compound as a high degree of purity relative to the raw products from which the chemical compounds are derived. One of skill in the art will readily recognize that any chemical compound, even after purification, may contain a "contaminant" to a greater or lesser degree. Accordingly, although the purified chemical compounds have been "purified", absolute purity may not be necessarily be obtained, without significant sacrifice of yield.

Figure 1:
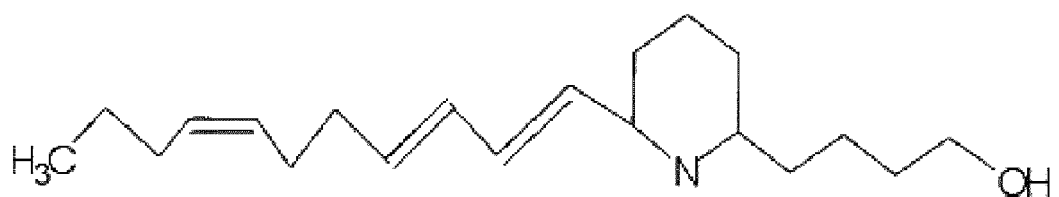
FIG. 1 depicts the chemical structure of the purified toxin according to the present invention. The figure depicts a piperidine structure with two substituents R1 and R2 along carbon 2 and 6 of the ring structure.

The term "euglenophycin" refers to a chemical compound having the structure as depicted in FIG. 1. The compound is an alkaloid and refers to an organic compound containing at least one nitrogen atom and a heterocyclic compounds in the form of a piperidine ring.

Toxin Identification and Purification

Episodic algal bloom samples were examined for sources of toxic algal bloom events. Water samples were examined by light microscopy (100-400×) to identify plankton present. Potentially toxic species were isolated and grown in sterile media then toxicity assessed by HPLC/MS or bioassays.

Unialgal isolates of *Euglena sanguinea* (isolated as a clonal culture from a North Carolina fish kill event) were grown in an environmental chamber in sterile AF6 media at 27° C. on a 14:10 light:dark photoperiod at 35 µmol photons $m^{-2}$ $s^{-1}$. Cell pellets were harvested from semi-continuous exponential-phase cultures-typically 35-50 L of media was harvested in each grow-out. For each harvest, media was filtered using 10 µm screening and cells were pelleted by centrifugation at 2800 RPM for 10 minutes then immediately frozen at −80° C.

An elutropic solvent fractionation scheme was used to extract toxin from cell biomass based on solvent defined polarity. Cell pellets were thawed in the dark, sonicated, then water, methanol, acetone and hexane, and were used to sequentially solubilize cellular components with cytotoxicity of each fraction was assessed using $GH_4C_1$ rat pituitary tissue culture cell lines. Stock cultures of rat pituitary ($GH_4C_1$) cells were maintained Ham's F10 medium supplemented with 15% horse serum and 2.5% fetal bovine serum (FBS). The cultures were incubated at 37° C. with 5% $CO_2$ and 95% air. Samples exhibiting cytotoxic activity were subjected to further purification using HPLC.

The toxic solvent extracts were subjected to HPLC analytical fractionation. Bioassay guided fractionation was used in all phases of separation to track sample activity and cytotoxic and/or ichthyotoxic extracts were identified. HPLC purification was carried out using a WATERS HPLC system (WATERS 2767 Sample Manager, 1525 Binary Pump, 510 pump, WATERS 2996 PDA and a WATERS ZQ Single Quadrature Mass Detector outfitted with an active flow splitter, switching valve using MASS LYNX software (Waters Corporation, Milford, Mass.). The HPLC/MS method was a water/acetone gradient with 0.2% TFA in both solvents. Extract was loaded onto a Phenomenex (Phenomenex Corporation, Torrance, Calif.) C18 LUNA 3 µm particle size, 250×4.6 mm column. The flow scheme conditions were: 1 mL/min flow rate, 90:10 Water/acetone (hold for 2 minutes). This was followed by a linear gradient over 20 minutes to 100% acetone. The acetone was held for 3 minutes prior to original flow conditions. Column temperature was held at 35° C.

After the development of HPLC/MS purification methodology the major toxic isomer (>80% of toxin present) was produced in sufficient quantities for NMR analysis (Bruker DMX 500 MHz NMR equipped with a gradient triple resonance 5 mm probe). Using a series of 1- and 2D NMR experiments ($^1$H, $^{13}$C, APT, COSY, HSQC, HMBC and NOESY) the molecular structure of the toxin was characterized.

NMR and mass spectral analysis provided unambiguous identification of the novel toxin. Re-exposure of fish to the toxin resulted in fish mortalities confirming bioactivity of the elucidated component. The euglenoids in culture appear to form the toxin independently of growth phase. This may suggest functionality as a preformed defense mechanism.

The methanol and acetone cell extracts displayed similar cytotoxic and ichthyotoxic activity. HPLC analysis of these extracts confirmed that the same compounds were present in both solvent fractions. Subsequent cell mass toxin extraction methodology was carried out with only acetone extraction (3×) followed by syringe filtration. This acetone extract was further purified using repeated acetone extraction and mass fractionated HPLC/MS.

The isolated toxin is a relatively non-polar compound exhibiting maximal absorbance at 238 nm in the UV spectral region. Purification was difficult as several stereo and molecular isomers were present. Active fractions exhibited a strong mass fingerprint at 288 amu which was subsequently shown to be the molecular ion minus an OH functionality (lost as $H_2O$). MS analyses provided a mass fingerprint common to all of the bioactive fractions (288 $[MH-H_2O]^+$; 306 $MH^+$) confirming the isomeric nature of the toxic substances. The toxin exists as a 2.6 disubstituted piperidine ring (FIG. 1). The major isomer was shown to have a cis-configuration with respect to C2 and C6, with minor components including trans configuration. COSY experiments on NMR revealed the presence of four stereoisomers under two chiral centers. At this time, only relative stereochemistry is known (Table 1).

TABLE 1

NMR results from euglenophycin analyses.

| Position | $^{13}C$ | APT Multiplicity | Selected H | J | NOESY |
|---|---|---|---|---|---|
| 1 | | | | | |
| 2 | 67.3 | CH | | | |
| 3 | 22 | $CH_2$ | * | | |
| 4 | 31.2 | $CH_2$ | | | |
| 5 | 30.7 | $CH_2$ | | | |
| 6 | 63.9 | $CH_2$ | * | | |
| 7 | 31 | $CH_2$ | | | |
| 8 | 23.7 | $CH_2$ | | | |
| 9 | 22.4 | $CH_2$ | | | |
| 10 | 51.9 | $CH_2$ | | | |
| 11 | 125.6 | CH | 5.45 dd | 9 Hz | Trans |
| 12 | 137.2 | CH | 6.32 dd | 9 Hz | Trans |
| 13 | 129.5 | CH | 6.11 dd | 10 Hz | Trans |
| 14 | 137.6 | CH | 5.8 m | | Trans |
| 15 | 32.6 | $CH_2$ | | | |
| 16 | 32 | $CH_2$ | | | |
| 17 | 129.9 | CH | 5.38 | 1.8 Hz | Cis |
| 18 | 130.9 | CH | 5.28 | 1.8 Hz | Cis |
| 19 | 34.5 | $CH_2$ | | | |
| 20 | 22.6 | $CH_2$ | | | |
| 21 | 13.9 | $CH_3$ | | | |

* NOESY demonstrated enhancements for H2 & H6 defining Cis relative stereo chemistry The Euglenoid toxin as described herein can be produced by: (a) culturing a Euglena sanguinea in a growth media to produce Euglenoid toxin therein; (b) separating a first fraction of organic compounds including said Euglenoid toxin from said growth media; (c) separating a second fraction consisting essentially of said Euglenoid toxin from said first fraction by chromatography with porous silica beads.

Growth Studies of Clonal Euglenoid Cultures

Clonal isolates of three Euglena sanguinea strains and Euglena viridis, Euglena granulata, and Euglena splendens were grown in AF6 media at 28° C. on a 14:10 L:D cycle. Culture were sampled every 3-5 days for growth rates estimation, and a single mid-exponential phase end point was used to determine toxicity of the other species.

Clonal isolates of five representative cyanoprokaryote, diatom, and green algae were grown in BG11 media at 28 C on a 14:10 L:D cycle. At mid-exponential phase growth, 1 mL aliquots of each culture was transferred to 96-well plates. Carrier solvent (control) and euglenophycin toxin was added to three of more replicate vials (at 0, 300 ppb, 3 ppm, and 30 ppm) and growth was monitored for five days.

The following examples are intended to further illustrate the invention, without any intent for the invention to be limited to the specific embodiments described therein. All patents and publications cited herein are incorporated by reference.

Example 1

Cytotoxicity Against Mammalian Tissue Cell Cultures $GH_4C_1$ rat pituitary cells as prepared supra, were exposed to euglenophyin. Specifically, Euglenga sanguinea cells were lyophilized to be dried and then extracted with 200 ml of dichloromethane. The solution was sonicated followed by decanting all solvent leaving the resulting cell mass. The cell mass was transferred with 100 g Iatrabeads along with 200 ml dichloromethane and rotoevaporated to dryness. The dry extract was then eluted through a column of clean Iatrabeads with a plurality of solvents as indicated in Table 2. Of the seven fractions, three fractions displayed activity against $GH_4C_1$ rat pituitary cells.

TABLE 2

| Solvent | $GH_4C_1$ rat pituitary cells activity |
|---|---|
| 100% Toluene | No |
| 50%-%0% Toluene-Ethyl Acetate | Yes |
| 100% Ethyl Acetate | Yes |
| 50%-50% Ethyl Acetate-Acetone | Yes |
| 100% Acetone | No |
| 50%-50% Acetone-Methanol | No |
| 100% Methanol | No |

Example 2

Allelopathy Against Tissue Cell Cultures

Figure 2:
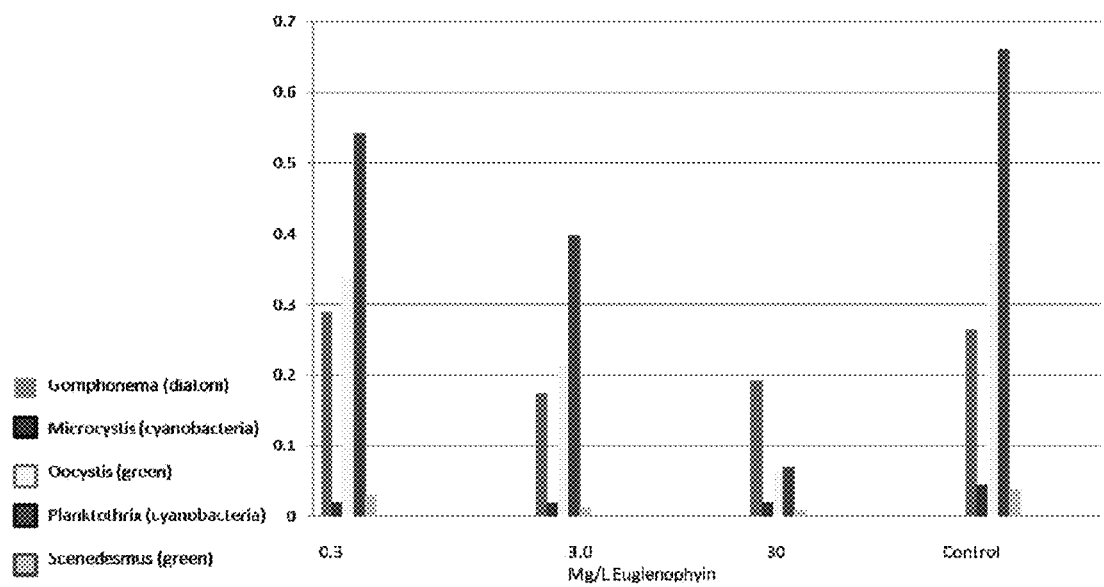
FIG. 2 depicts day two of chlorophyll concentration of a plurality of algal species as a function of euglenophycin exposure at 0, 0.3, 3 and 30 mg/L concentrations.

To evaluate the euglenophycin against the growth rate of selected algal taxa. Cultures of five algal species grown in batch culture were exposed to the euglenophycin. The culture include Microcystis aeruginosa (cyanobacteria), Planktothrix (cyanobacteria), Gomphonema parvum (diatom), Scenedesmus dimorphus (green algae), and Oocystis polymorpha (green algae). The cultures were grown using 14:10 hour L:D cycles, in BG11 culture media. When the alga reached exponential phase, the cells were dispensed into Falcon 96-well tissue culture plates and were dosed with euglenophycin at 0, 0.3, 3 and 30 mg/L concentrations. Solvent blanks (acetone) were included in the control test. Readings of chlorophyll a were made on a BMG Labtech FLUOstar Omega spectrometer daily for four days. FIG. 2 depicts that all cultures were negatively affected by euglenophycin exposure.

Example 3

Toxicity Against Adenocarcinoma Cell Line, Ht-29

Figure 3:
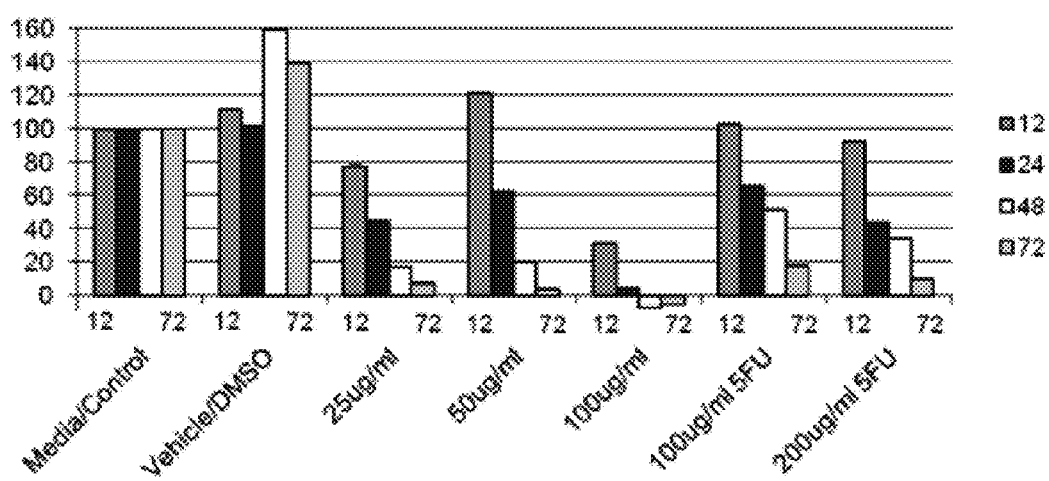
FIG. 3 depicts a graph of HT29 cell line in response to the euglenophycins, dimethyl sulfoxide, and 5-fluorouracil.

ATCC culture collection HTB-38, also termed Ht-29, was tested against the Euglena sanguinea derived toxin as indicated in FIG. 3. Specifically, cancer cells were grown to mid-exponential growth phase, aliquots were added to tissue culture plates with carrier (control) and varying euglenophycin toxin (25, 50, 100 mg/L final concentration), with and without 5-fluorouracil and maintained in dimethyl sulfoxide. Growth was monitored by colorimetric change associated with respiration using MTS or MTT assay).

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. A purified and isolated compound extracted from *Euglena sanguinea*, wherein the compound has the structure:

and wherein the compound is toxic against plant and mammalian cells.

2. The compound of claim 1 wherein the compound is an alkaloid with a molecular weight of about 288 Da to about 306 Da.

3. A composition comprising the compound according to claim 2, wherein the compound is present at a concentration range of about 0.3 mg to about 30 liter of the composition.

4. The compound of claim 1 wherein the composition is toxic against algal cells.

5. A method of controlling undesirable algal bloom comprising contacting a waterway with an herbicidal composition comprising an effective amount of an isolated and purified compound having the structure:

6. The method of claim 5 wherein the composition is isolated from *Euglena sanguines*.

7. The method of claim 5, wherein the compound is present in a concentration range of about 0.3 mg per liter of the herbicidal composition to about 30 mg per liter.

8. The method of claim 5, wherein the undesirable algal bloom is selected from the group consisting of: *Microcystis aeruginosa, Planktothrix, Gomphonema parvum, Scenedesmus dimorphus*, and *Oocystis polymorphs*.

* * * * *